United States Patent
Xie et al.

(10) Patent No.: US 11,181,633 B2
(45) Date of Patent: Nov. 23, 2021

(54) LOADED-TO-FRAME DETECTION EQUIPMENT AND METHOD FOR BACKFILL GROUTING OF SHIELD TUNNEL

(71) Applicant: Tongji University, Shanghai (CN)

(72) Inventors: Xiongyao Xie, Shanghai (CN); Biao Zhou, Shanghai (CN); Yunxiang Zhou, Shanghai (CN); Hui Qin, Shanghai (CN); Yifan Chen, Shanghai (CN)

(73) Assignee: Tongji University, Shanghai (CN)

( * ) Notice: Subject to any disclaimer, the term of this patent is extended or adjusted under 35 U.S.C. 154(b) by 0 days.

(21) Appl. No.: 16/410,625

(22) Filed: May 13, 2019

(65) Prior Publication Data

US 2019/0330984 A1    Oct. 31, 2019

Related U.S. Application Data

(63) Continuation of application No. PCT/CN2018/082763, filed on Apr. 12, 2018.

(30) Foreign Application Priority Data

Jun. 21, 2017    (CN) .......................... 2017104727288

(51) Int. Cl.
*G01S 13/88* (2006.01)
*E21D 11/10* (2006.01)
(Continued)

(52) U.S. Cl.
CPC ............ *G01S 13/885* (2013.01); *E21D 11/10* (2013.01); *E21F 17/18* (2013.01); *E21D 9/003* (2013.01); *E21D 11/105* (2013.01)

(58) Field of Classification Search
CPC ....... E21D 9/003; E21D 11/003; E21D 11/10; E21D 11/105; E21D 9/06; G01S 7/03;
(Continued)

(56) References Cited

FOREIGN PATENT DOCUMENTS

| CN | 103123252 | 5/2013 |
|----|-----------|--------|
| CN | 103573269 | 2/2014 |
| CN | 104989423 | 10/2015 |

(Continued)

OTHER PUBLICATIONS

Zhou, Binzhong & Shen, B. & Guo, H & Wallace, D. (2006). Time-Lapse Ground Penetrating Radar Survey for Grout Injection Trial at Baal Bone Colliery. (Year: 2006).*

(Continued)

*Primary Examiner* — Matthew M Barker
(74) *Attorney, Agent, or Firm* — Garvey, Smith & Nehrbass, Patent Attorneys, L.L.C.; Vanessa M. D'Souza; Seth M. Nehrbass

(57) ABSTRACT

The present invention relates to a loaded-to-frame detection equipment for backfill grouting of a shield tunnel, including an automatic loaded-to-frame transmission apparatus, a ground penetrating radar, and an intelligent backfill grouting processing and analysis software. The equipment is integrated by using software and hardware, and can implement real-time visual detection of a backfill grouting layer in a shield construction process. The loaded-to-frame automatic transmission apparatus mainly includes a track, a synchronous belt, a transmission mechanism, a servo machine, and a drive and reducer; and a new air-coupled radar detection apparatus is carried on the loaded-to-frame automatic transmission apparatus and is installed on a shield frame. With the shield performs tunneling, circular detection on a grouting body of the shield and visual layered display of the grouting body are implemented.

10 Claims, 3 Drawing Sheets

(51) Int. Cl.
*E21D 9/00* (2006.01)
*E21F 17/18* (2006.01)

(58) Field of Classification Search
CPC ............... G01S 13/885; G01N 33/383; G01N 2021/9548; G01N 22/02; B25J 5/02; E21F 17/00–18
See application file for complete search history.

(56) References Cited

FOREIGN PATENT DOCUMENTS

| | | |
|---|---|---|
| CN | 105545325 | 5/2016 |
| CN | 107120120 | 9/2017 |
| JP | 0274796 | 3/1990 |
| KR | 101281242 | 7/2013 |

OTHER PUBLICATIONS

X. Y. Xie, Y. F. Chen and B. Zhou, "Data processing of backfill grouting detected by GPR in shield tunnel and research on equipment of GPR antenna," 2016 16th International Conference on Ground Penetrating Radar (GPR), Hong Kong, China, 2016, pp. 1-5, doi: 10.1109/ICGPR.2016.7572690. (Year: 2016).*

X. Y. Xie, Y. F. Chen and B. Zhou, "Data Processing of Backfill Grouting Detected by GPR in Shield Tunnel and Research on Equipment of GPR Antenna" Conference poster, 2016 16th International Conference on Ground Penetrating Radar (GPR), Hong Kong, China, Jun. 13-16, 2016. (Year: 2016).*

International Search Report for International Patent Application No. PCT/CN2018/082763.

\* cited by examiner

LOADED-TO-FRAME DETECTION EQUIPMENT AND METHOD FOR BACKFILL GROUTING OF SHIELD TUNNEL

This application is a continuation application of International Patent Application Serial No. PCT/CN2018/082763, filed Apr. 12, 2018, which itself claims priority to Chinese patent application 2017104727288, filed Jun. 21, 2017. The aforementioned applications are hereby incorporated herein by reference and priority is hereby claimed.

TECHNICAL FIELD

The present invention belongs to the field of backfill grouting and cavity detection during construction of a shield tunnel, and specifically, to a loaded-to-frame detection equipment and method for backfill grouting of a shield tunnel.

BACKGROUND

In recent years, as China has increased infrastructure investment, China's traffic construction has rapidly developed, and the construction and research of highway tunnels, especially long tunnels, has also rapidly developed. At present, China is the country that has the largest number of tunnel projects in the world and the country whose tunnel projects are the most complex and have developed fastest. Based on a principle "head and tail protection and frequent grouting" in shield construction, radar detection equipment is researched and developed to implement detection of a backfill grouting thickness of a shield. Peripheral deformation control is of great significance to ensure construction and surrounding environment safety. At present, synchronous grouting of a shield tunnel is an important measure to control stratum deformation and protect existing tunnels, bridges, and surrounding environments. However, such grouting is not easy to control; and for shield tail structure void estimation and grouting parameter setting, there is no experience to follow. In addition, during curve crossing, it is difficult to perform quality control of tunnel construction, thereby easily causing a correction gap. If improper control is performed, ground surface settlement is caused during the construction stage, and existing tunnels and bridges are deformed greatly. In an operation stage, water leakage and mud leakage in a tunnel will be caused or a partial tunnel structure will be damaged; or an internal structure (such as the subway track) of a tunnel will be vertically distorted and deformed, thereby affecting the normal operation of the tunnel, and causing potential threats to the safety of the tunnel structure and the safety and comfort of the subway train operation. Further, the operation of various structures around and on the ground is affected, causing huge economic losses and even serious socially adverse effects. Conventionally, the synchronous grouting amount is generally determined according to manual experience or manually, and a shape and a filling degree of a grouting body at a rear part of a segment cannot be determined effectively, and therefore the grouting operation cannot be effectively guided in real time. Therefore, it is necessary to conduct special research on grout mechanics and diffusion characteristics, prediction and detection of actual grouting injection amount, real-time detection of an actual grouting effect, and the like.

At present, quality detection of backfill grouting of a shield in China mainly includes manual field measurement and recording performed after tunnel construction is completed. Then, subsequent processing is performed indoors. At this time, the ground surface settlement has occurred for a long time, and a disease caused by a grouting defect has generated significant economic losses, and therefore the detection significance is relatively small at this time. In addition, manual detection is easily restricted by field conditions and has relatively low stability. Equipment for real-time automatic detection of backfill grouting urgently needs to be developed.

SUMMARY

An objective of the present invention is to provide loaded-to-frame detection equipment for backfill grouting of a shield tunnel.

The loaded-to-frame detection equipment for backfill grouting of a shield tunnel proposed in the present invention preferably includes a ground penetrating radar 1, a servo controller 2, a drive motor and reducer 3, a transmission mechanism 4, a radar acquisition box 5, a support 6, an assembly type track 7, a belt wheel 9, and a conveyor belt 10, a support plate 11, where the assembly type track 7 is of an arched structure, the ground penetrating radar 1 is carried above the assembly type track 7 through the support plate 11, and the ground penetrating radar 1 can move along the assembly type track at a uniform speed and perform discontinuous detection at equal time intervals through the support plate 11; the transmission mechanism 4 and the drive motor and reducer 3 are fastened to one side of the assembly type track 7, the transmission mechanism 4 is connected to the drive motor and reducer 3, the servo controller 2 is fastened onto a side surface of the assembly type track 7, the servo controller 2 is connected to the drive motor and reducer, and several belt wheels 9 are fastened below the assembly type track 7; one end of the conveyor belt 10 is connected to the support plate 11, the other end thereof bypasses above the assembly type track 7, passes the transmission mechanism 4, and passes through the several belt wheels 9 in sequence, and after arriving at a bottom part of the other side of the assembly type track 7, the conveyor belt 10 bypasses above the other side of the assembly type track 7 and is connected to the support plate 11, so that the conveyor belt forms a closed loop; the radar acquisition box 5 is fastened to the support 6, and the radar acquisition box 5 is preferably connected to the ground penetrating radar 1 by using a coaxial cable; several shield machine assembly interfaces 8 are disposed below the assembly type track 7; the loaded-to-frame detection equipment for backfill grouting of a shield tunnel is carried on a shield machine frame through the shield machine assembly interfaces 8; and under control of the servo controller 2, the transmission mechanism is driven by the drive motor and reducer 3, the transmission mechanism drives the conveyor belt 10 and the belt wheel 9, and the conveyor belt 10 drives, by driving the support plate 11, the ground penetrating radar 1 to perform a circular motion.

In the present invention, an antenna detection frequency of the carried radar is preferably between 300 MHz and 900 MHz, so as to improve a detection effect of a backfill grouting body.

In the present invention, according to front clearance and operation requirements of a shield machine, a movement range of the ground penetrating radar 1 can preferably satisfy a detection requirement of 20° to 360°, a motion mode of the ground penetrating radar 1 includes moving at a uniform speed and performing discontinuous pausing at an equal time interval, and each time a shield performs tunneling by one ring, the ground penetrating radar 1 performs circular grouting detection of the shield.

In the present invention, the radar acquisition box 5 is preferably connected to an operation room computer by using a network cable; and visual radar image analysis software is configured on the operation room computer for analysis to implement visual layered display of a grouting body.

In the present invention, the assembly type track is formed by connecting several assembly type track sections in sequence.

Beneficial effects of the present invention are as follows:

(1) Achievement of real-time detection of backfill grouting of a shield tunnel, and backfill grouting construction level is improved: the detection equipment is carried in the front of a first frame of a shield machine and moves following the shield machine, so as to implement real-time automatic detection of backfill grouting slurry; grouting parameter adjustment and grouting slurry supplementation are implemented to assist backfill grouting construction, so as to improve the backfill grouting construction.

(2) Improvement of the detection quality of backfill grouting: in the present invention, an arc track is designed, and the ground penetrating radar performs circular detection along the track. This improves detection stability and a positioning effect of a radar wave compared with manual detection.

(3) Safety convenience: detection personnel can adjust a detection range of a fracture surface by increasing a number of assembly type sections, and an entire detection process is performed automatically and has characteristics of safety and convenience.

(4) High image processing real-time performance: after the detection is completed, a form of a grouting body can be synchronously displayed by using self-developed visual software, so as to shorten indoor processing time of previous manual detection.

DETAILED DESCRIPTION OF EMBODIMENTS

The following further describes the present invention with reference to the accompanying drawings.

Figure 1:
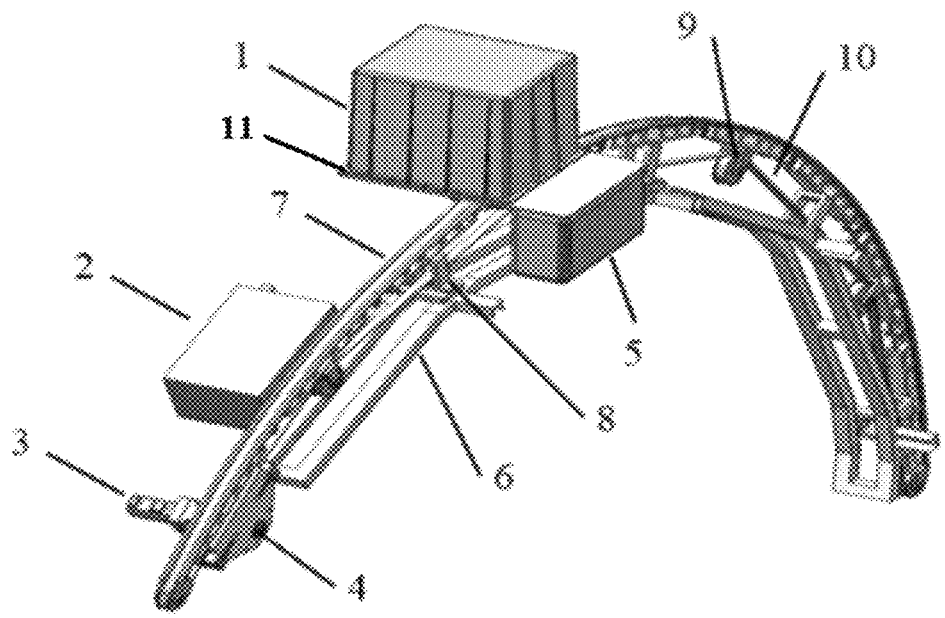
FIG. 1 a schematic structural diagram of loaded-to-frame detection equipment for backfill grouting of a shield tunnel developed by the present invention.

Embodiment 1: As shown in FIG. 1, an apparatus includes a ground penetrating radar 1, a servo controller 2, a drive motor and reducer 3, a transmission mechanism 4, a radar acquisition box 5, a support 6, an assembly type track 7, shield machine assembly interfaces 8, a belt wheel 9, a conveyor belt 10, and a support plate 11. The ground penetrating radar 1 is connected to the conveyor belt 10 by using a support plate 11, the conveyor belt performs a circular motion through traction by the drive motor and reducer 3 and the transmission mechanism 4, and a motion mode thereof is controlled by the servo controller 2. The ground penetrating radar 1 obtains a radar signal and transmits the radar signal to the radar acquisition box 5 by using a coaxial cable, and transmits, preferably by using a network cable, the radar signal to an operation room computer to perform data analysis.

Figure 2:
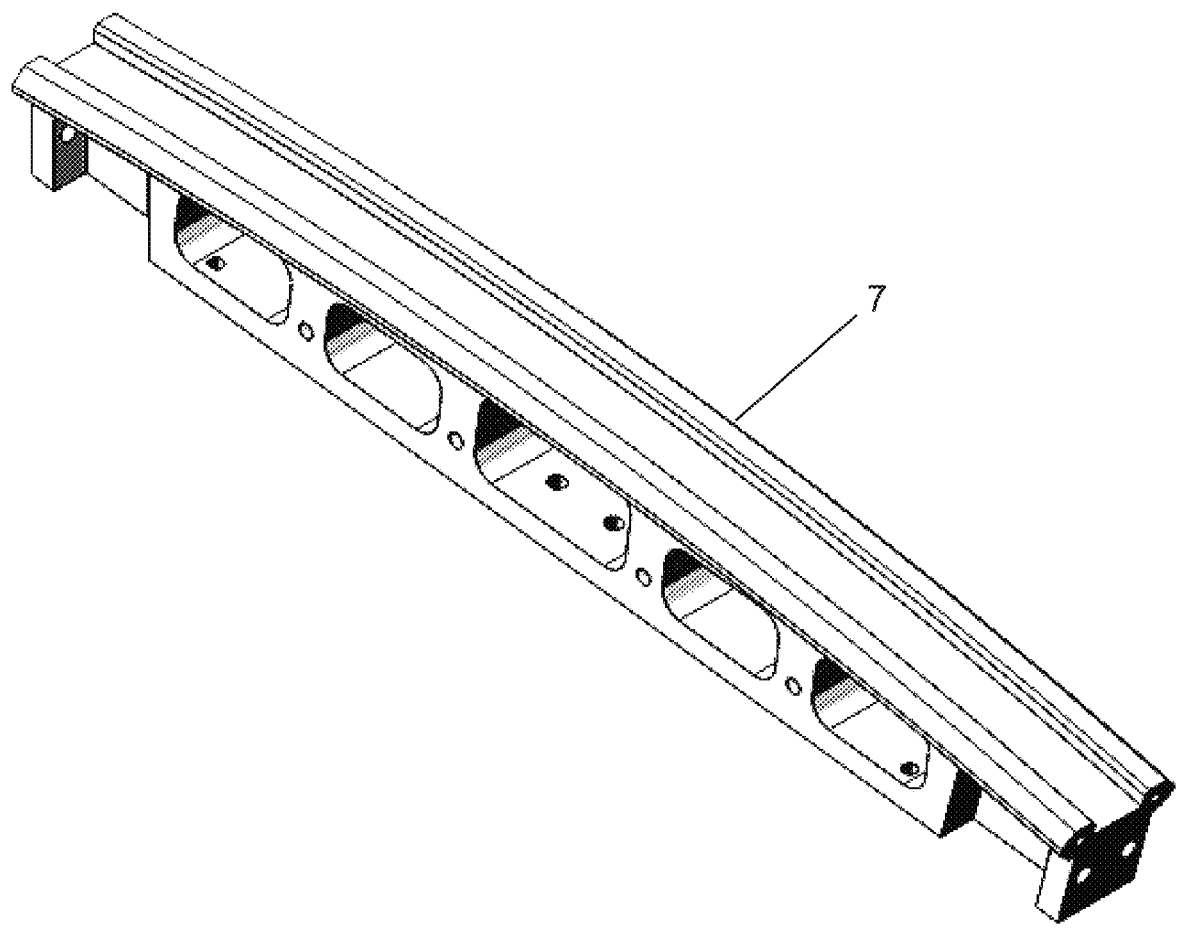
FIG. 2 is a diagram of a section of an assembly type track.

FIG. 2 is a diagram of a section of an assembly type track according to the present invention. A number of phases required for the section of the assembly type track are calculated according to a requirement of an actual detection angle. The assembly type track 7 is formed by connecting several assembly type track sections in sequence.

Figure 5:
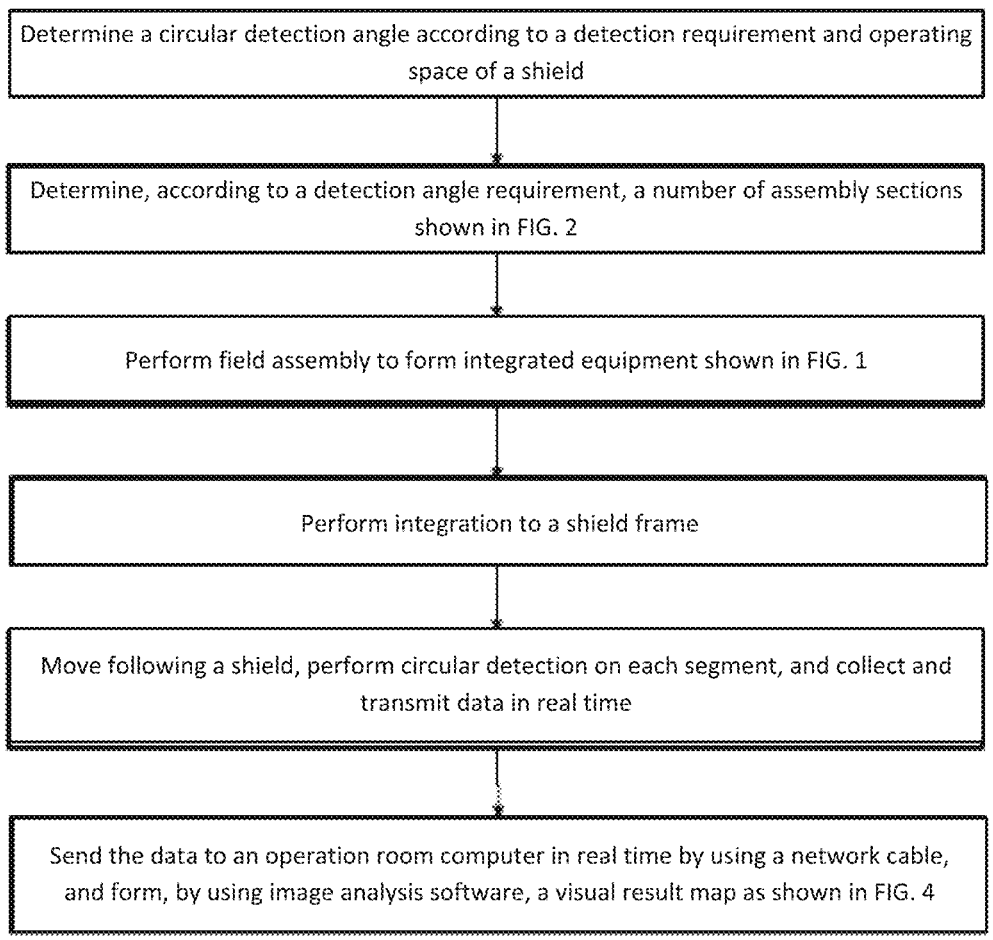
FIG. 5 is a path diagram of an implementation of a preferred embodiment of the present invention.

Referring to FIG. 5, in the present invention, a circular detection angle is first determined according to a detection requirement and operating space of a shield, and the angle is preferably controlled between 20° to 360°. The number of required sections is calculated according to a requirement of an actual detection angle and a length of the assembly section shown in FIG. 2, and field assembly is performed to form integrated equipment shown in FIG. 1. After the assembly is completed, the integrated equipment shown in FIG. 1 is carried on a shield machine frame through shield machine assembly interfaces 8, to form an integrated equipment.

Figure 3:
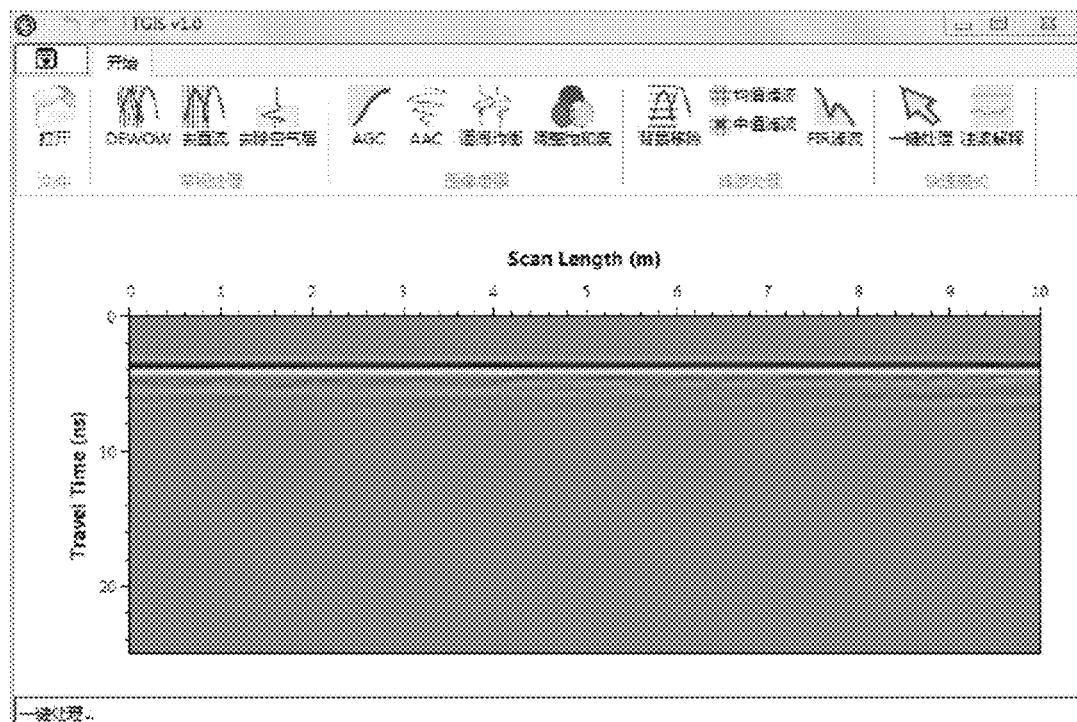
FIG. 3 is a diagram of real-time processing of a radar signal by a signal processing unit by comprehensively using methods such as DEWOW (dislodge/remove weight of window), direct current removal, air layer removal, background removal and filtering, AGC/ACC (Automatic Gain Control/Automatic Chroma Control), and track equalization.
Figure 4:
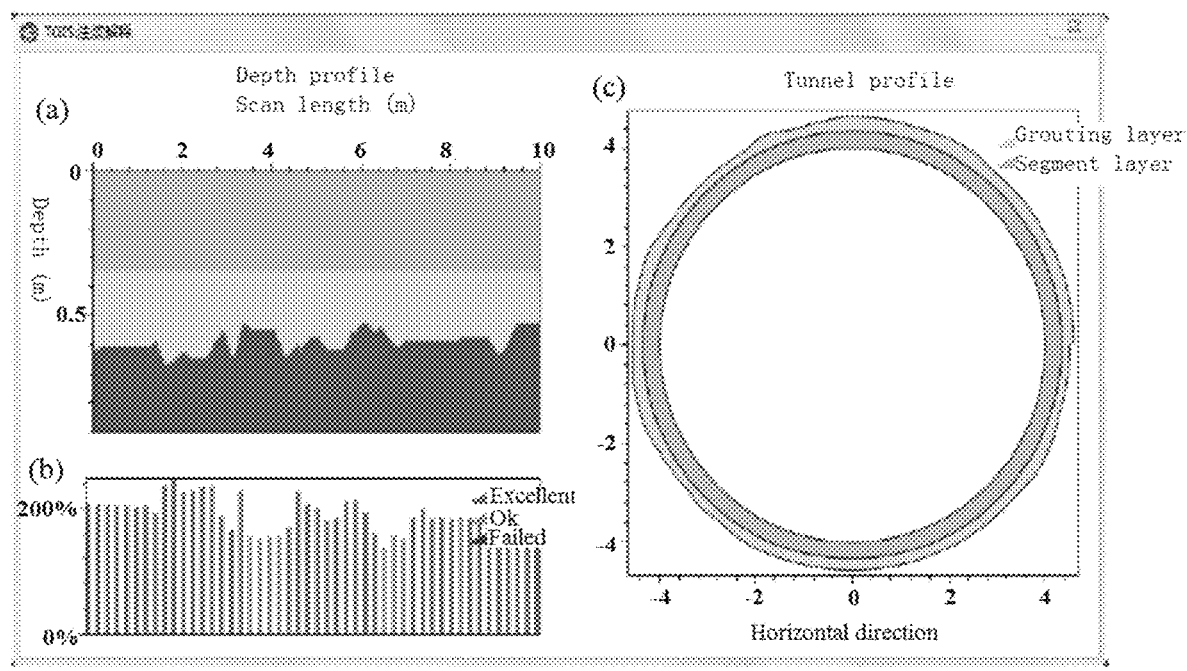
FIG. 4 is a visual display diagram of backfill grouting obtained through field detection, where (a) is an expanded view of layer thicknesses of a grouting body and a soil layer at a segment; (b) is a grouting fullness coefficient diagram (a percentage in this figure is a ratio of an actual detection thickness of a grouting body to a designed value), and (c) is a visual display diagram of backfill grouting distribution.

The equipment may move following a shield after being integrated, and performs circular detection on each segment. In a detection process, a radar acquisition box 5 collects radar data and sends the radar data back to an operation room computer in real time, preferably by using a network cable. Real-time processing is performed on a radar signal in real time by a signal processing module shown in FIG. 3 by comprehensively using methods such as DEWOW (dislodge/remove weight of window), direct current removal, air layer removal, background removal and filtering, AGC/ACC (Automatic Gain Control/Automatic Chroma Control), and track equalization), so as to obtain a visual diagram of a grouting layer as shown in FIG. 4, where (a) is an expanded view of layer thicknesses of a grouting body and a soil layer at a segment; (b) is a grouting fullness coefficient diagram (a percentage in this figure is a ratio of an actual detection thickness of a grouting body to a designed value), and (c) is a visual display diagram of backfill grouting distribution.

| PARTS LIST | |
|---|---|
| 1 | ground penetrating radar |
| 2 | servo controller |
| 3 | drive motor and reducer |
| 4 | transmission mechanism |
| 5 | radar acquisition box |
| 6 | support |
| 7 | assembly type track |
| 8 | shield machine assembly interface |

-continued

| | PARTS LIST |
|---|---|
| 9 | belt wheel |
| 10 | conveyor belt |

What is claimed is:

1. A loaded-to-frame detection equipment for backfill grouting of a shield tunnel, comprising a ground penetrating radar, a servo controller, a drive motor and reducer, a transmission mechanism, a radar acquisition box, a support, a support plate, an assembly track, a belt wheel, and a conveyor belt, wherein the assembly track is of an arched structure, the ground penetrating radar is carried above the assembly track by means of the support plate, and the ground penetrating radar can move back and forth along the assembly track by means of the support plate; the transmission mechanism and the drive motor and reducer are fastened to one side of the assembly track, the transmission mechanism is connected to the drive motor and reducer, the servo controller is fastened onto a side surface of the assembly track, the servo controller is connected to the drive motor and reducer, and a plurality of belt wheels are fastened below the assembly track; one end of the conveyor belt is connected to the support plate, another end thereof bypasses above the assembly track, passes the transmission mechanism, and passes through the plurality of belt wheels in sequence, and after arriving at a bottom part of an other side of the assembly track, the conveyor belt bypasses above an other side of the assembly track and is connected to the support plate, so that the conveyor belt forms a closed loop; the radar acquisition box is fastened to the support, and the radar acquisition box is connected to the ground penetrating radar by using an coaxial cable; a plurality of shield machine assembly interfaces are disposed below the assembly track; the loaded-to-frame detection equipment for backfill grouting of a shield tunnel is carried on a shield machine frame through the shield machine assembly interfaces; and under control of the servo controller, the transmission mechanism is driven by the drive motor and reducer, the transmission mechanism drives the conveyor belt and the belt wheel, and the conveyor belt drives, by driving the support plate, the ground penetrating radar to perform a circular motion.

2. The loaded-to-frame detection equipment for backfill grouting of a shield tunnel according to claim 1, wherein an antenna detection frequency of the ground penetrating radar is 300 MHz to 900 MHz.

3. The loaded-to-frame detection equipment for backfill grouting of a shield tunnel according to claim 1, wherein according to front clearance and operation requirements of a shield machine, a movement range of the ground penetrating radar can satisfy a detection requirement of 20° to 360°, a motion mode of the ground penetrating radar comprises moving at a uniform speed and performing discontinuous pausing at an equal time interval, and each time a shield performs tunneling by one ring, the ground penetrating radar performs circular grouting detection of the shield.

4. The loaded-to-frame detection equipment for backfill grouting of a shield tunnel according to claim 1, wherein the radar acquisition box is connected to an operation room computer by using a network cable; and visual radar image analysis software is configured on the operation room computer for analysis to implement visual layered display of a grouting body.

5. The loaded-to-frame detection equipment for backfill grouting of a shield tunnel according to claim 1, wherein the assembly track is formed by connecting a plurality of track sections in sequence.

6. A loaded-to-frame detection method for backfill grouting of a shield tunnel, comprising steps of:
determining a circular detection angle according to a detection requirement and operating space of a shield machine;
determining a number of track sections according to the detection angle determined;
performing assembly in field to form the loaded-to-frame detection equipment according to claim 1;
mounting the loaded-to-frame detection equipment to a frame of the shield machine;
detecting each shield segment in circular direction, collecting and transmitting data to a computer by using a network cable in real time while moving with the shield machine; and
processing the data and forming a visual diagram of a grouting layer at the computer.

7. A loaded-to-frame detection method for backfill grouting of a shield tunnel, comprising steps of:
determining a circular detection angle according to a detection requirement and operating space of a shield machine;
determining a number of track sections according to the detection angle determined;
performing assembly in field to form the loaded-to-frame detection equipment according to claim 2;
mounting the loaded-to-frame detection equipment to a frame of the shield machine;
detecting each shield segment in circular direction, collecting and transmitting data to a computer by using a network cable in real time while moving with the shield machine; and
processing the data and forming a visual diagram of a grouting layer at the computer.

8. A loaded-to-frame detection method for backfill grouting of a shield tunnel, comprising steps of:
determining a circular detection angle according to a detection requirement and operating space of a shield machine;
determining a number of track sections according to the detection angle determined;
performing assembly in field to form the loaded-to-frame detection equipment according to claim 3;
mounting the loaded-to-frame detection equipment to a frame of the shield machine;
detecting each shield segment in circular direction, collecting and transmitting data to a computer by using a network cable in real time while moving with the shield machine; and
processing the data and forming a visual diagram of a grouting layer at the computer.

9. A loaded-to-frame detection method for backfill grouting of a shield tunnel, comprising steps of:
determining a circular detection angle according to a detection requirement and operating space of a shield machine;
determining a number of track sections according to the detection angle determined;
performing assembly in field to form the loaded-to-frame detection equipment according to claim 4;
mounting the loaded-to-frame detection equipment to a frame of the shield machine;

detecting each shield segment in circular direction, collecting and transmitting data to a computer by using a network cable in real time while moving with the shield machine; and processing the data and forming a visual diagram of a grouting layer at the computer.

10. A loaded-to-frame detection method for backfill grouting of a shield tunnel, comprising steps of:

determining a circular detection angle according to a detection requirement and operating space of a shield machine;

determining a number of track sections according to the detection angle determined;

performing assembly in field to form the loaded-to-frame detection equipment according to claim 5;

mounting the loaded-to-frame detection equipment to a frame of the shield machine;

detecting each shield segment in circular direction, collecting and transmitting data to a computer by using a network cable in real time while moving with the shield machine; and processing the data and forming a visual diagram of a grouting layer at the computer.

* * * * *